United States Patent [19]

Ohrem et al.

[11] Patent Number: 5,770,411
[45] Date of Patent: Jun. 23, 1998

[54] MICROBIAL PROCESS FOR THE PREPARATION OF DIHYDROXYACETONE WITH RECYCLING OF BIOMASS

[75] Inventors: Hans Leonard Ohrem, Weiterstadt; Frank Westmeier, Munster, both of Germany

[73] Assignee: Merck Patent Gesellschaft Mit Beschrankter Haftung, Darmstadt, Germany

[21] Appl. No.: 571,671

[22] Filed: Dec. 13, 1995

[30] Foreign Application Priority Data

Dec. 14, 1994 [DE] Germany .......................... 44 44 404.4

[51] Int. Cl.⁶ ................................ C12P 7/26; C12P 7/28; C12P 7/02
[52] U.S. Cl. ........................... 435/148; 435/150; 435/155
[58] Field of Search .................................... 435/148, 150, 435/155

[56] References Cited

U.S. PATENT DOCUMENTS 2,948,658 8/1960 Green ........................................ 195/43
4,076,589 2/1978 Charney ..................................... 195/49

OTHER PUBLICATIONS

Derwent Abstract 95–391458 Barbot et al RV2031123 (Mar. 1995).

Derwent Abstract 91–046452/07 Balogh et al HU–206743–B (Dec. 1992).

*Primary Examiner*—Herbert J. Lilling
*Attorney, Agent, or Firm*—Millen, White, Zelano, & Branigan, P.C.

[57] ABSTRACT

The invention relates to a microbial process for the preparation of dihydroxyacetone, the conversion of glycerol to dihydroxyacetone being carried out using a microorganism having active dehydrogenase with complete or partial recycling of biomass which is no longer capable of growth, and corresponding addition of preliminary cultures fully capable of growth.

26 Claims, 2 Drawing Sheets

FIG. I

MICROBIAL PROCESS FOR THE PREPARATION OF DIHYDROXYACETONE WITH RECYCLING OF BIOMASS

SUMMARY OF THE INVENTION

The invention relates to a microbial process for the preparation of dihydroxyacetone. The conversion of glycerol to dihydroxyacetone is carried out using a microorganism having active dehydrogenase with periodic partial recycling of biomass, which is no longer capable of growth, and the addition, coordinated with the production cycles, of preliminary cultures fully capable of growth.

The production of dihydroxyacetone (DHA) from glycerol by suitable microorganisms has long been generally known. Since dihydroxyacetone is a valuable feedstock for the chemical and pharmaceutical industry, there is a permanent interest in providing the compound on an industrial scale in the simplest and most economical manner possible. Consequently, in the course of the years, variations in the culture and fermentation conditions have been performed with the aim of constantly improving the yield (see, for example, U.S. Pat. No. 2,948,658, U.S. Pat. No. 4,076,589, DD 230,713 and DD 253,836).

The fermentation broths of the prior art contain glycerol for the most part in a 5–20% concentration, which in some few cases is fed as a supplement. Additives such as glucose, sorbitol, yeast extracts, corn steep water and salts conventional in bacterial culture are contained in the fermentation batch generally in concentrations between less than 1% and up to 15% and the pH during the microbial synthesis of dihydroxyacetone generally varies between 5 and 7. The dihydroxyacetone yields quoted in the prior art vary on average between 10 and 150 g/l for a culture or reaction time of 20 to 70 h, depending on the type of fermentation (batch process or completely continuous fermentation).

In the microbial DHA synthesis of the prior art, attention was paid in particular to the fact that apparently a decisive role must be assigned to both the amount of starting material (glycerol) and also of synthesized product (dihydroxyacetone), since both compounds, if they are present at relatively large concentrations in the fermentation broth, adversely affect growth and/or productivity of the microorganism used (see, for example, Claret et al. (1992), Current Microbiol. 25 (3):149). Thus, the cells of the culture used, in the course of the production process, suffer irreversible damage owing to the accumulating dihydroxyacetone, so that, after a production period of about 20 to 30 hours, they are no longer capable of multiplication, or only to a very restricted extent, and must be ejected from the actual production process. This has the consequence that a completely new culture must be used for the next production cycle. Corresponding preliminary cultures must then generally be transferred to the production fermenter in which the culture in turn is to grow for a limited time. The growth in the production stage is necessary to achieve a satisfactory productivity. Therefore, nutrient salts and complex nitrogen sources, such as yeast extract, must also be provided in sterilized form on this scale. This is responsible for a large part of the raw material costs and for problems in the work-up, isolation and quality assurance of the end product. Moreover, in this conventional procedure, the space-time yield of the product (in g/l×h) of the overall system is tightly coupled to the growth rate in the production fermenter, which in turn, as mentioned above, is limited by the dihydroxyacetone formed. In addition, unproductive preliminary culture times represent a not inconsiderable portion of the total process time required.

Decoupling of growth and actual production would therefore be desirable.

It has now been established that, on the one hand, microorganisms having active dehydrogenase, on culturing in the absence of their actual substrate glycerol and in the presence of monosaccharides or sugar alcohols, over a relatively long period, do not lose their ability to multiply. On the other hand, after addition of glycerol and the accumulation of DHA which progresses in accordance with the enzymatic reaction, although they lose their ability to grow, they do not lose their actual catalytic activity.

It has now been found that these observations can serve as a basis for novel and advantageous preparation of DHA, which can also be applied on an industrial scale, using microorganisms in a batch process. According to this, the biomass which is no longer capable of growth is no longer removed from the production process after a completed production cycle, but remains in the fermenter in whole or at least in part and serves there as a charge for the subsequent DHA production cycle.

The invention thus relates to a process for the preparation of dihydroxyacetone by dehydrogenation of glycerol by means of microorganisms having active dehydrogenase in a plurality of production cycles, which can be characterized in that the biomass which is no longer capable of growth and which is obtained after one production cycle is reused in whole or in part for the respective following production cycle.

If some, preferably 10 to 30%, of the biomass not capable of growth is removed after one cycle, it is supplemented by fresh preliminary culture capable of growth. According to the invention, in this case, the culture to be added is grown in a glycerol-free medium in which thus no cell-damaging DHA can accumulate. If an amount of glycerol is present in the medium, the amount should not lead to an accumulation of dihydroxyacetone greater than 10 g/l.

The invention thus also relates to a corresponding process in which a preliminary culture capable of growth is added to the subsequent production cycle or a production cycle following this cycle, which preliminary culture is preferably grown in a glycerol-free medium and makes up 10 to 30%, in particular 10–20%, of the total biomass.

The invention relates in particular to a process in which the preliminary culture capable of growth is added to one of the subsequent production cycles in such a manner that the preliminary culture is added either after each or after every second to fifth cycle, the addition of the preliminary culture needing to be controlled in such a manner that the yield of dihydroxyacetone does not under any circumstances fall below a value of 4 g/l h.

According to the invention, all those known microorganisms are suitable which are capable of oxidizing because of active dehydrogenases and recognize glycerol as a substrate. Especially the genera Acetobacter and Gluconobacter can be used therefor, in particular *Gluconobacter oxydans* is preferably suitable. Examples of generally accessible *Gluconobacter oxydans* strains are the strains ATCC 621 (DSM 50049, NCIB 621, NRRLB72), DSM 2343 (ATCC 621H, NCIB 8036), ATCC 9324 (NCTC 4739), ATCC 23771 (NCIB 3734, NCTC 3734) and DSM2003. See also J. Med. Lab. Technol., 20:26–33 (1963); J. Biol. Chem., 174:273 (1948); J. Bacteriol., 125:1163–1171 (1976); J. Bacteriol., 45:183 (1943); U.S. Pat. No. 3,234,105; Nature, 192:683 (1961); and J. Gen. Microbiol., 24:34 (1961).

The necessary preliminary cultures capable of growth are preferably grown in a glycerol-free culture medium. Carbon sources which serve are monosaccharides or sugar alcohols, in particular sorbitol, mannitol, fructose or glucose, the sugar alcohols, in particular sorbitol, being preferred. Glycerol is deliberately avoided as an energy source and carbon source, in order to preferably achieve no DHA formation in this pure growth phase. The content of sugar alcohols in the culture medium is according to the invention preferably about 50–300 g/l, especially about 100–150 g/l.

The culture medium for the preliminary culture preferably contains, in addition to the conventional nutrient salts known for such purposes, a yeast extract as complex nitrogen source. However, other known nitrogen sources, such as amino acids or corn steep liquor, can be used for the process according to the invention, or else yeast extracts which have been enriched with amino acids. The content of yeast extract or amino acids is according to the invention preferably about 1–10 g/l, especially about 3–6 g/l.

The biomass of the preliminary culture is transferred to the production fermenter and admixed with nutrient medium for the first production cycle. The nutrient medium contains suitable salts, for example, those used conventionally, for these purposes and appropriate nitrogen sources as already used in growing the preliminary culture, in particular yeast extracts. In addition, the substrate is now added. The starting content of glycerol is preferably about 20–100 g/l, especially about 30–60 g/l, in a particularly preferred embodiment about 50 g/l. During a production cycle, which according to the invention lasts generally about 10–30, preferably about 15–25 hours, the glycerol content is preferably maintained by constant replenishment at a concentration of about 2–50 g/l, especially about 5–35 g/l. The respective glycerol content in the reaction suspension can be determined by generally known methods, for example, by means of sampling and glycerol determination by chromatographic determination. Establishment of a substantially constant glycerol content has proved to be highly beneficial for the space-time yield, but in this context is ultimately not necessarily essential to the invention. The pH is preferably kept constant during fermentation at a defined pH of about 3.8–4.8. Preferably, a pH of about 4.0–4.5 is set. The pH is preferably set by a calcium hydroxide solution. The use of calcium ions, for example in the form of calcium chloride, in any case has a favorable effect on the yield. The content of calcium ions is preferably about 1–5 g/l. The fermentation temperature is according to the invention preferably about 28°–34° C., especially about 30°–32° C. The fermentation broth is aerated in a conventional manner with air or oxygen.

In a first variant of the process, after the first production cycle, the entire biomass separated off, which is generally no longer capable of multiplication, is not destroyed, but completely returned to the production cycle. In these cases, the fermenter is not charged with culture medium but solely with calcium-ion-containing substrate solution (e.g., about 1 g/l–5 g/l calcium chloride and about 5 g/l–200 g/l glycerol), which does not need to be sterilized. The glycerol content is also kept constant here, as described above, by additional feed. In the subsequent cycles also, a similar procedure can be followed. Since in this manner, in long-term operation, the biomass increases from cycle to cycle, it is advisable to eject some of the biomass. In this process variant some of the specific productivity (product formation per unit time) is deliberately dispensed with, but the space-time yield can be set to almost any desired value by increasing the biomass, the maximum oxygen transfer rate of the aeration system being, at all events, a method-specific upper limit.

After about five cycles, an initially slow, later more rapidly occurring loss of catalytic activity (conversion of glycerol to DHA) is generally observed. According to the invention, therefore, for instance after every third production cycle, some of the biomass, preferably about 10–30%, in particular about 10–20%, is replaced by fresh preliminary culture fully capable of growth. In this case, it is advisable to supply culture medium wholly or partially again to the fermenter, since this leads to slightly increased yields. However, for reasons of process economics, at least for some production cycles, calcium-ion-containing substrate solution can be used exclusively. The addition, after certain production cycles, of the preliminary culture capable of growth should expediently be performed when the yield of DHA threatens to fall below a value of 4 g/l h. When fermentations are performed below this value for a relatively long period, the economic efficiency of the process is restricted.

In a second process variant, the fresh preliminary culture is added in principal after every cycle or at least after every second cycle. This variant produces the highest yields of DHA in association with still advantageous process economics, improved with respect to the prior art, whereas the process economics, the yields in this case being somewhat under the maximum which may be achieved.

The dihydroxyacetone formed can be isolated and purified from the fermenter solution by standard methods.

By the process according to the invention, DHA yields of preferably about 8–14 g/l ×h or about 160–250 g/l×cycle (1 cycle=approximately 20 hours) can be achieved.

The advantages of the process according to the invention in comparison with the known batch processes of the prior art are:

lower raw material costs, savings of time and energy in sterilization and preparation of the fermenter, simplified and quantitatively improved work-up of the product, for example, higher membrane filter flow rates (filtration of the solution enriched with product), less variation in quality due to fewer accompanying materials (caused by the lower amounts of media required), reduced contamination of the product by sulfate ash (from media, equivalent to the sum of the inorganic salts), the space-time yield can be set freely in a broad range, and avoidance of waste and reduced loading of the sewage treatment plant.

DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views, and wherein.

DETAILED DESCRIPTION

FIG. 1

Figure 1:
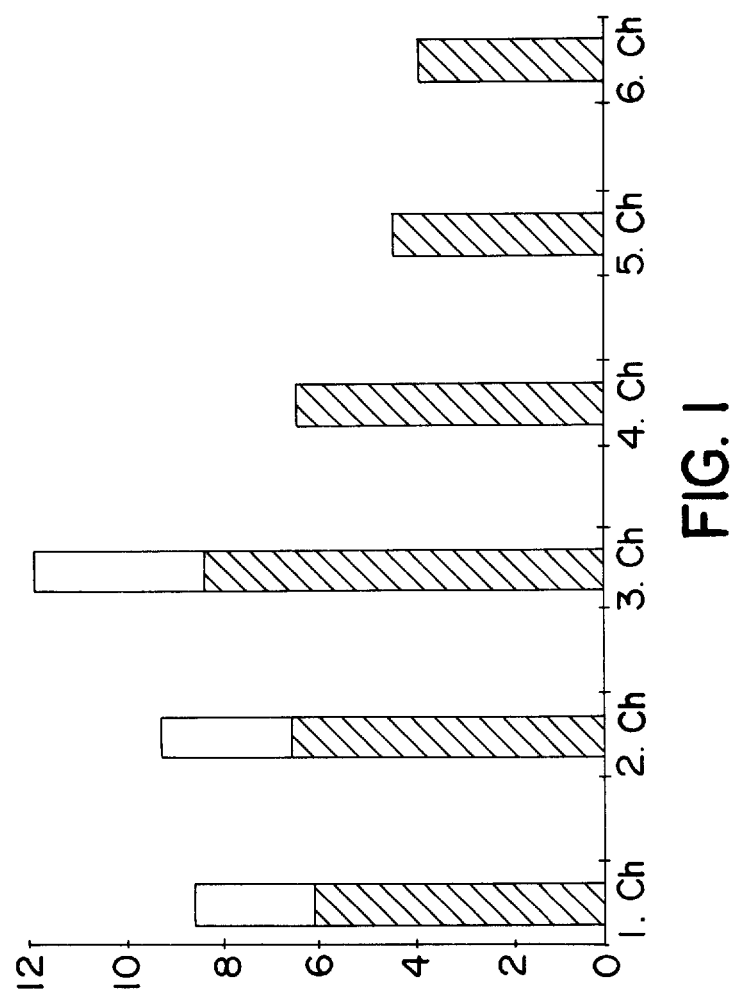
FIG. 1 graphically illustrates space-time yields for the production cycles of Examples 1 and 2.

Space-time yield as a measure of the productivity in DHA fermentations according to Example 1 (1st to 3rd production cycle) and according to Example 2 (3rd to 6th production cycle) are shown in FIG. 1. By feeding fresh preliminary cultures, the productivity can be increased or maintained. Without feeding the preliminary culture, the biomass initially loses a relatively large amount of productivity, but later only little. On the x-axis are given the batch numbers (production cycles), and on the y-axis the space-time yields in g/l h of DHA. The hatched areas indicate the permanent portion and the white areas indicate the growth-associated portion.

FIG. 2

Figure 2:
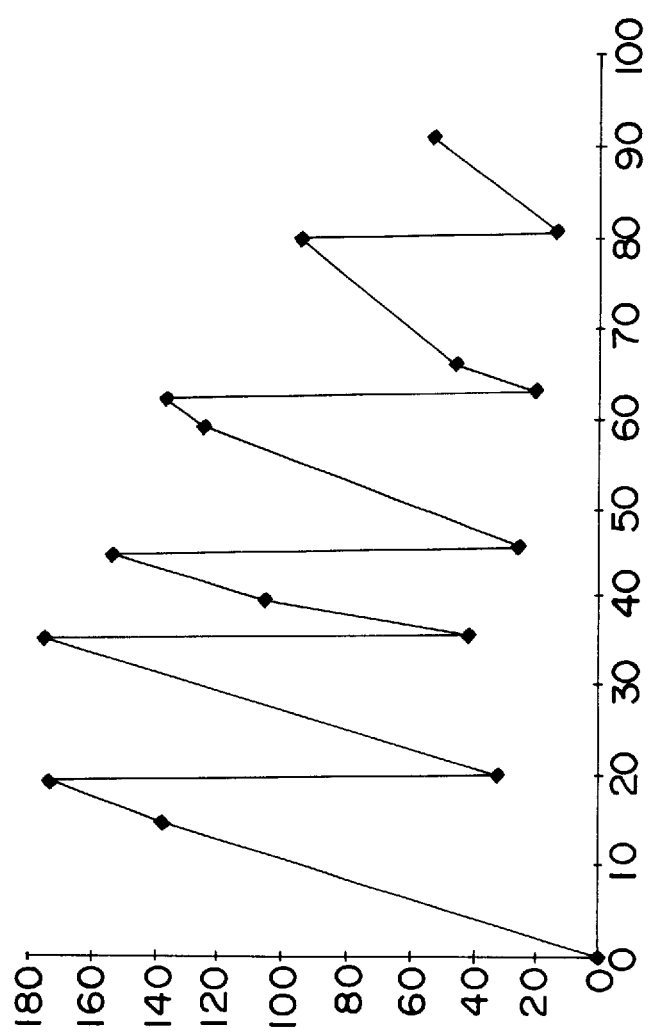
FIG. 2 graphically illustrates dihydroxyacetone concentration as a function of time.

FIG. 2 shows the course of DHA concentration in the six production cycles as in FIG. 1. On the x-axis is given the fermentation time (h) and on the y-axis the DHA concentration (g/l).

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding German application P 44 44 404.4, are hereby incorporated by reference.

EXAMPLES

Example 1

For the conversion of glycerol to DHA, 100 of a medium are made up having the following composition:

| | |
|---|---|
| Sorbitol | 150 g/l |
| Yeast extract | 5 g/l |
| Ammonium sulfate | 2 g/l |

The solution is sterilized (20 minutes, 120° C.) and, after cooling, is inoculated with 5 to 10 of a preliminary culture with dense growth of the bacterium *Gluconobacter oxydans* (ATCC 621; 2.5 g of dry matter/l).

With strong aeration (50 l/min) and vigorous mixing, the bacterial culture is allowed to grow for a period of approximately 10 to 15 h. The biomass thus obtained is transferred as a preliminary culture to a 1000 l fermenter which contains 700 of a previously sterilized nutrient medium having the following composition:

| | |
|---|---|
| Glycerol | 50 g/l |
| Yeast extract | 5 g/l |
| Ammonium sulfate | 2 g/l |

With vigorous aeration (300 /min) and mixing, the glycerol content is kept at a concentration of 25 to 35 g/l by constant replenishment. In this manner, glycerol is oxidized to DHA for 10 to 25 hours.

After the fermentation has been terminated, the biomass situated in the fermenter is separated off by microfiltration (0.2 $\mu$m) and 90% thereof is returned to the fermenter. The filtrate is passed to a further product treatment. The fermenter is now charged to a volume of 700 l with calcium chloride substrate solution (3 g/l of calcium chloride and 50 g/l of glycerol) which had not been sterilized in advance. After a newly prepared preliminary culture suspension (in nutrient medium) has been transferred to the fermenter, the next production cycle is started. The procedure described is repeated after each production cycle. After the first cycle, 180 g/l of DHA are obtained, after the second cycle 200 g/l and after the third cycle 210 g/l (FIG. 1).

Example 2

One production cycle is carried out similarly to Example 1. In the subsequent production cycle, the fermenter is charged not with nutrient solution, but with 10% glycerol solution and 3% calcium chloride solution, to 800. In addition, 100% of the biomass from the preceding production cycle is fed. By replenishment, the glycerol content is likewise kept at 5 to 35 g/l. In this manner, three to five production cycles can be carried out without feeding nutrient solution and preliminary cultures. Owing to decreasing productivity, the fermenter is started again with fresh preliminary culture at the latest after the fifth production cycle (FIG. 2).

Example 3

One production cycle is carried out similarly to Example 1. For the subsequent cycle, the fermenter is now charged, not with calcium substrate solution, but with nutrient medium. Fresh culture is added after each further cycle. After the first cycle, 190 g/l of DHA are obtained, after the second cycle 220 g/l and after the third cycle 235 g/l.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for the preparation of dihydroxyacetone by dehydrogenation of glycerol by means of microorganisms having sufficient dehydrogenase activity to dehydrogenate glycerol, in a plurality of production cycles, the improvement wherein:

said microorganisms are cultured in a culture medium containing monosaccharides or sugar alcohols to form preliminary culture, and wherein the amount of glycerol, if present in said culture medium, does not lead to an accumulation of dihydroxyacetone greater than 10 g/l, after each production cycle is completed, biomass which is no longer capable of growth is reused in whole or in part for the next production cycle, and preliminary culture capable of growth is added to at least one subsequent production cycle in such a manner that the yield of dihydroxyacetone does not fall below 4 g/l h.

2. A process according to claim 1, wherein said after the first production, all of the biomass is reused and the second production cycle is performed, without the addition of additional growth medium, in the presence of aqueous calcium-ion-containing substrate solution, and at a pH of 3.8–4.8.

3. A process according to claim 1, wherein after each production cycle 70 to 90% of said biomass is reused.

4. A process according to claim 1, wherein said preliminary culture is grown in a glycerol-free medium.

5. A process according to claim 4, wherein said culture medium contains at least one sugar alcohol.

6. A process according to claim 1, wherein the amount of preliminary culture added to any subsequent production cycle makes 10–20% of the total biomass.

7. A process according to claim 1, wherein production cycles with addition of preliminary culture capable of growth follow corresponding production cycles without addition of preliminary culture.

8. A process according to claim 1, wherein *Gluconobacter oxydans* is used as said microorganism.

9. A process according to claim 1, wherein preliminary culture capable of growth is added after each production cycle.

10. A process according to claim 1, wherein preliminary culture is added after every second to fifth production cycle.

11. A process according to claim 5, wherein the concentration of sugar alcohol in said culture medium is 50–300 g/l.

12. A process according to claim 5, wherein said culture medium further contains yeast extract, amino acids or corn steep liquor as complex nitrogen source.

13. A process according to claim 1, wherein, during production cycles, the glycerol content is maintained at a concentration of 2–50 g/l.

14. A process according to claim 1, wherein, during dehydrogenation, the pH is maintained at 4.0–4.5.

15. A process according to claim 1, wherein, during dehydrogenation, calcium-ion content is 1–5 g/l.

16. A process according to claim 2, wherein said calcium-ion-containing substrate solution contains 1–5 g/l calcium chloride and 5–200 g/l glycerol.

17. A process according to claim 1, wherein the amount of preliminary culture added to any subsequent production cycle makes up 10–30% of the total biomass.

18. A process according to claim 1, wherein the initial culture of microorganisms and/or one or more cultures added to the fermentation broth during said process is grown in a medium wherein the amount of glycerol present does not lead to an accumulation of more than 10 g/l of dihydroxyacetone.

19. A process according to claim 1, wherein the initial culture of microorganisms and/or one or more cultures added to the fermentation broth during said process is grown in a glycerol-free medium.

20. A process according to claim 5, wherein said culture medium contains sorbitol.

21. A process according to claim 12, wherein said culture medium contains yeast extract or amino acids in an amount of 1–10 g/l.

22. A process according to claim 13, wherein the glycerol content is maintained at a concentration of 5–35 g/l.

23. A process according to claim 1, the dihyroxyacetone yield is is 8–14 g/l xh.

24. A process according to claim 1, wherein said microorganisms are of the genera Acetobacter or Gluconobacter.

25. In a process for the preparation of dihydroxyacetone by dehydrogenation of glycerol by means of microorganisms having sufficient dehyrogenase activity to dehydrogenate glycerol, in a plurality of production cycles, the improvement wherein:

said microorganisms are cultured in a culture medium containing monosaccharides or sugar alcohols, to form preliminary culture, and wherein the amount of glycerol, if present in said culture medium, does not result in a cell-damaging amount of hidroxy acetone accumulation, after each production cycle is completed, biomass which is no longer capable of growth is reused in whole or in part for the next production cycle, and preliminary culture capable of growth is added to at least one subsequent production cycle in such a manner that the yield of dihydroxyacetone does not fall below 4 g/l h.

26. In a process for the preparation of dihydroacetone by dehydrogenation of glycerol by means of microorganisms having sufficient hydrogenase activity to dehydrogenate glycerol to dihydroacetone, in a plurality of production cycles, the improvement wherein before starting the production cycles the microorganisms are cultivated in the absence of glycerol and in the presence of monosaccharides or sugar alcohols to form preliminary culture, the biomass obtained after one production cycle which is no longer capable of growth is reused only partially for the subsequent production cycle, and preliminary culture capable of growth is added to said subsequent production cycle and/or a production cycle following said subsequent production cycle.

* * * * *